United States Patent [19]

Houng

[11] Patent Number: 5,958,686
[45] Date of Patent: Sep. 28, 1999

[54] SIMPLE PCR TECHNIQUE FOR DETECTING AND DIFFERENTIATING BACTERIAL PATHOGENS

[75] Inventor: Huo-Shu H. Houng, Burtonsville, Md.

[73] Assignee: The United States of America as represented by the Secretary of the Army, Washington, D.C.

[21] Appl. No.: 08/738,922

[22] Filed: Oct. 28, 1996

[51] Int. Cl.⁶ .............................. C12Q 1/68; C12P 19/34; C07H 21/04
[52] U.S. Cl. .......................... 435/6; 435/91.2; 536/24.32; 536/24.33
[58] Field of Search ................... 435/91.2, 6; 536/24.33, 536/24.32

[56] References Cited

U.S. PATENT DOCUMENTS

| | | | |
|---|---|---|---|
| 4,992,364 | 2/1991 | Sansonetti et al. | 435/6 |
| 5,041,372 | 8/1991 | Lampel et al. | 435/6 |
| 5,298,302 | 3/1994 | Atlas et al. | 435/600 |
| 5,492,811 | 2/1996 | Gilson et al. | 435/6 |
| 5,648,481 | 7/1997 | Parodos et al. | 536/24.32 |

OTHER PUBLICATIONS

Frankel, G. et al. (1990) Detection of Shigella in Feces Using DNA Amplification. *J. Infect. Dis.* 161: 1252–1256.
Sethabutr et al. Detection of Shigellae and enteroinvasive *Escherichia coli* by amplification of the invasion plasmid antigen h DNA sequence in patients with dysentery J. Infectious deseases, vol. 167, p. 458– 61, 1993.
Klena et al. Function of the rfb gene cluster and the rfe gene in the synthesis of O antigen by *Shigella dysenteriae* 1, vol. 9(2), pp. 393–402, 1993.
Morona et al. Characterization of the rfc Region of *Shigella flexneri* vol. 176(3), pp. 733–747, 1994.
Houng, Search report accession No.: U34305, Jan. 1, 1996.

*Primary Examiner*—Kenneth R. Horlick
*Attorney, Agent, or Firm*—Charles H. Harris; John Francis Moran

[57] ABSTRACT

A simple polymerase chain reaction procedure is described for the detection and differentiation of Shigella from other pathogenic *Escherichia coli* isolates, such as EIEC and EPEC. Serotype specific primers derived from the rfc genes of different Shigella strains are used to identify the most prominents Shigella serotypes, such as *S. sonnei, S. flexneria* 1 through 5, and *S dysenteriae* 1. More than 95% of Shigellosis cases reported could be identified by the serotype specific primers described.

11 Claims, 1 Drawing Sheet

SIMPLE PCR TECHNIQUE FOR DETECTING AND DIFFERENTIATING BACTERIAL PATHOGENS

INTRODUCTION

Bacillary dysentery, caused mainly by Shigella and other genetically related enteroinvasive *Escherichia coli* (EIEC), is responsible for a substantial proportion of acute diarrheal diseases worldwide [Keusch, G. T. and Formal, S. B. Shigellosis. In:: Warren, K. S., and Mahamond, A. A. F., editors. (1984) *Tropical and Geographic Medicine,* 1st ed. New York: McGraw-Hill p723–726; Taylor D. N. et al. (1986) *J. Infect Dis.* 153:1131–1138]. Dysentery is characterized by painful abdominal cramps and frequent defecation of blood and mucus attributed to penetration and destruction of colonic epithelia by invasive infections. Detection of Shigella and enteroinvasive *Escherichia coli* from drinking water had been recently reported [Echeverria P. et al. (1992) *J. Infect. Dis..* 165:144–147). However, a natural ecological niche for the causative bacteria of dysentery is still unknown.

There are four species of Shigella defined as serotype A, *S. dysenteriae* with 12 serotypes; serotype B, *S. flexneri* with 6 serotypes and 13 subserotypes; serotype C, *S. boydii* with 18 serotypes; and serogroup D, *S. sonnei* with a single serotype. Shigellae are normally isolated and identified in fecal specimens of infected patients through bacteriological culturing followed by biochemical tests and serological studies. The traditional identification process is not only time consuming but also requires an experienced laboratory technician who is able to accurately isolate and identify bacterial colonies cultivated from clinical samples. DNA probes, ial (invasion-associated locus) and ipaH, have been developed and used to identify dysenteric causing bacteria by either nucleic acid hybridization, or PCR amplification [Frankel G. et al. (1990) *J. Infect Dis.* 161: 1252–1256; Sethabutr O. et al. (1993) *J. Infect Dis.* 167:458–461 ;Sethabutr O. et al. (1994) *J. Diarrhoeal Dis Res.* 12:265–269]. All these techniques involve multiple centrifugations and lengthy incubations with different enzymes, such as lysozyme and proteinase K. Furthermore, none of these previously developed systems could be used to differentiate between Shigella isolates and EIEC strains or between different serotypes of Shigella. Identification of specific serotypes is important since antibiotic treatment selection for dysenteric pathogens differs according to the causative pathogen.

Therefore, there is a need for a simple diagnostic assay which is able to detect Shigella and identify prominent Shigella serotypes from clinical samples.

SUMMARY

The present invention is directed to a method and means that satisfies this need. In this application is described a simple polymerase chain reaction (PCR) procedure applied directly on a clinical sample using serotype specific primers for differentiating Shigella serotypes from other pathogenic *E. coli* isolates such as enteroinvasive *E. coli* (EIEC), and enteropathogenic *E. coli* (EPEC) and detecting and identifying the most prominent Shigella serotypes. More than 95% of Shigella cases reported to could be identified by the serotype specific primers described in this application.

Immunity to Shigella infections is largely species specific (serotype-specific) and is determined by the O-side chains of lipopolysaccharide (LPS). Previous studies indicate that O-antigens of Shigella play a major role in protection against homologous strains, as seen in animal and human challenges [Dupont, H. L. et al. (1969) *J. Infect. Dis.* 119: 296–299; Formal, S. B. et al. (1966) *J. Bact.* 92:17–22]. Early observations indicating that O-specific side chains might also be involved in pathogenicity were based on the fact that most bacteria isolated from intestinal infections are smooth. The O-antigen of Shigella is encoded by genes organized as the rfb operon [Klena, J. D. and C. A. Schnaitman (1993) *Mol. Microbiol.* 9: 393–402; Macpherson, D. F. et al.(1991) *Mol. Microbiol.* 5:1491–1499; Viret, J-F et al. (1993) *Mol. Microbiol.* 7:239–252; Watanabe, H. and A. Nakamura (1986) *Infect. & Immun.* 53:352–358] and a specific rfc gene which encodes the O-antigen polymerase able to polymerize O-antigen subunits into long LPS chains. It is known that the rfc shows very little homology with all the other gene sequences deposited in the Genbank database [Collins, L. V. and J. Hackett (1991) *J. Bact.* 173: 2521–2529; Klena, J. D. and C. A. Schnaitman (1993) *Mol. Microbiol.* 9: 393–402; Morona, R. et al.(1994) *J. Bact.* 176:733–747]. Thus, homologous rfc sequences are present only in organisms that assemble identical, or even closely related, O-antigen saccharides into LPS chains of closely related serotypes, such as *S. flexneri* type 1 through type 5.; the O-LPS of *S. flexneri* type 6 does not share any structure or genetic homology with the other serotypes of *S. flexneri* [Cheah, K.-C. et al.(1991) *FEMS Microbiol. Lett.* 83: 213–218]. Similarly, the rfc sequences of *S. sonnei* and *S. dysenteriae* 1 are not homologous with the rfc genes of other Shigella species.

Thus, the primers employed for PCR amplification in this invention are derived from sequences of rfc genes of different Shigella species and serotypes and can specifically differentiate *S. sonnei, S. flexneri* 1–5, and *S. dysenteriae* 1 based on the specific PCR product sizes. The rfc primer sequences described in this invention can specifically detect and identify the most prevalent Shigella serotypes (the serotypes recognized and amplified by the primers of the present invention contribute to more than 95% of Shigelloses reported to the Center for Disease Control, Atlanta, Ga. CDC ,MMWR, Oct. 6, 1995, vol. 43) and do not yield non-specific PCR products even in the presence of closely related *E. coli,* or other Shigella serotypes. PCR amplification using the rfc-specific primers described in this invention can be utilized to rapidly detect and identify serogroups, or serotypes of Shigella. The entire process requires only 2–4 hours in contrast to 48–72 hours required for conventional bacterial culture, biochemical, serological, or DNA—DNA hybridization tests.

Therefore, it is one object of the present invention to describe a method for detecting and identifying different serotypes of Shigella. The method of the present invention utilizes PCR oligonucleotide primer sets derived from the rfc genes designed to yield PCR products of diffrerent molecular mass when used in a polymerase chain reaction on clinical samples.

More particularly, it is an object of the present invention to describe a method for detecting and identifying different serotypes of Shigella using PCR primer sets from *S. sonnei* (Genbank #U34305) (SEQ ID NO: 1 and SEQ ID NO: 2), *S. flexneri* 2a (EMBL #X71970) (SEQ ID NO: 3 and SEQ ID NO: 4), and *S. dysenteriae* 1 (Genbank #L07293) (SEQ ID NO: 5 and SEQ ID NO: 6).

It is another object of the present invention to provide a method for preparing stool samples for clinical diagnosis using PCR. The method comprises diluting the stool sample and boiling the diluted sample. The sample can then be used for PCR amplification or alternatively, the sample can be subjected to centrifugation to pellet large particles and the supernatant containing the template used for PCR.

It is a further object of the present invention to provide primers for use in PCR assays on a sample for the purpose of identifying and serotyping Shigella present in the sample.

It is yet another object of the invention to provide a method for designing primers for use in identifying other bacterial pathogens using sequences of rfc genes also known as LPS polymerase. Other bacterial pathogens which contain an rfc gene include, but are not limited to, *Salmonella typhimurium, Salmonella enterica, Pseudomonas aeruginosa, E. coli,* to name a few.

BRIEF DESCRIPTION OF THE DRAWINGS

These and other features, aspects, and advantages of the present invention will become better understood with regard to the following description, appended claims, and accompanying drawings where

DETAILED DESCRIPTION

Figure 1:
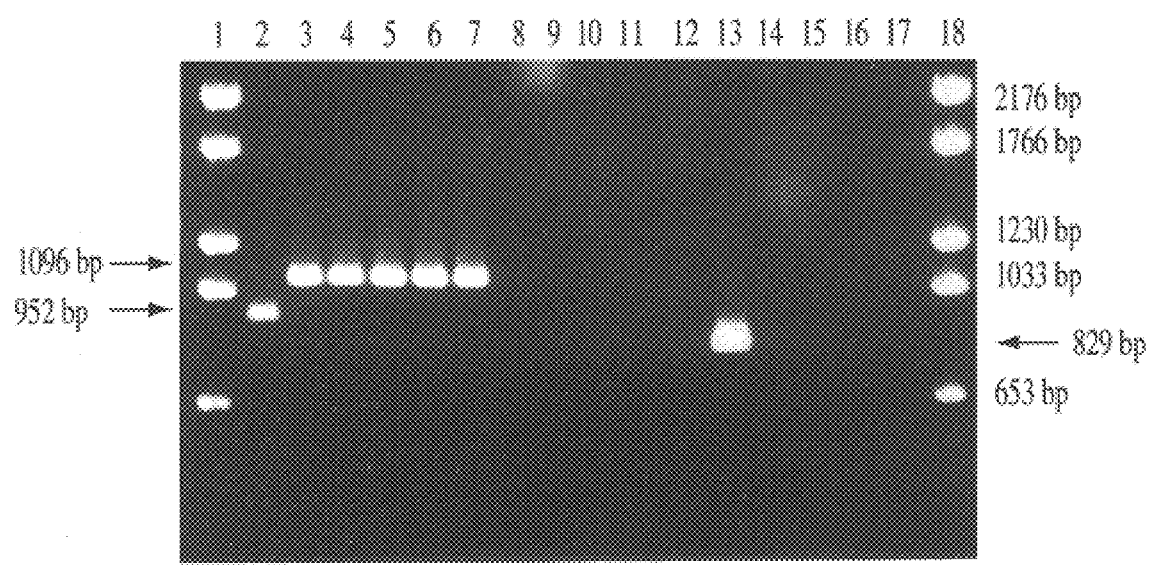
FIG. 1 represents an agarose gel showing PCR products derived from 100 μl PCR reaction mixture (1× PCR buffer, 1.0 mM $MgCl_2$, 0.1 mM dNTP's, 2.0 μM for each of oligonucleotides in Table 1) containing 2 μl of boiled overnight cultures. Lane 1 and 18. DNA molecular weight standard; 2. *S. sonnei;* 3. *S. flexneri* type 1; 4. *S. flexneri* type 2; 5. *S. flexneri* type 3; 6. *S. flexneri* type 4; 7. *S. flexneri* type 5; 8. *S. flexneri* type 6; 9. *S. boydii* 1; 10. *S. boydii* 2; 11. *S. boydii* 4; 12. *S. boydii* 10; 13. *S. dysenteriae* 1; 14. *S. dysenteriae* 3. 15. *S. dysenteriae* 4; 16 *E. coli* DH1; 17 water control. PCR amplification was carried out at: 95° C., 3 minutes; 30 cycles of 95° C., 30 seconds; 55° C., 30 seconds; 72° C., 1 minute.

The present invention describes a method for detecting and identifying Shigella in a clinical sample said method comprising using sets of primers in a polymerase chain reaction (PCR) which result in a PCR product of different molecular mass depending on the presence of a certain Shigella species and serotype in the sample.

Novel primers were designed from rfc gene sequences of different species of Shigella obtained from the Genbank database. As was discussed earlier, the rfc gene encodes the polymerase which is responsible for the addition of subunits of saccharides to form the O-antigen of the bacteria. Each species and serotype of Shigella contains an O-antigen that is specific and different than the O-antigen of other species and serotypes of Shigella. The primers were chosen such that each primer set can detect a specific species and serotype of Shigella, evidenced by a PCR product of certain molecular mass, which can be detected by resolving the PCR products on a gel and visualizing the products.

The method for the detection and identification of Shigella in a sample is comprised of the following steps:

(i) preparing the sample for a polymerase chain reaction;
(ii) contacting said sample with
  (a) at least four different nucleotide triphosphates,
  (b) a first primer cocktail that hybridizes to Shigella DNA of different Shigella species and serotypes of Shigella, and
  (c) an enzyme with polynucleotide synthetic activity, under conditions suitable for the hybridization and extension of primers by said enzyme, whereby a first DNA product is synthesized with said Shigella DNA as a template therefor, such that one or more duplex molecule(s) is formed;
(iii) denaturing said duplex to release said first DNA product from said Shigella DNA;
(iv) contacting said first DNA product with a reaction mixture comprising
  (a) at least four different nucleotide triphosphates,
  (b) a second primer cocktail that hybridizes to said first DNA product, and
  (c) an enzyme with polynucleotide synthetic activity, under conditions suitable for the hybridization and extension of said second primer by said enzyme, whereby a second DNA product is synthesized with said first DNA product as a template therefor, such that a duplex is formed;
(v) denaturing said second DNA product from said first DNA product;
(vi) repeating steps ii–v for a sufficient number of times to achieve linear production of said first and second DNA products;
(viii) fractionating said first and second DNA products generated from said Shigella DNA; and
(ix) detecting said fractionated products of step viii.

This assay is amenable for use with "samples" such as biological samples derived from a human or other animal source (such as, for example, blood, stool, sera, urine, saliva, tears, biopsy samples, histology tissue samples, PAP smears, moles, warts, etc.) including samples derived from a bacterial or viral preparation, as well as other samples (such as, for example, agricultural products, waste or drinking water, milk or other processed foodstuff, air, etc.).

The assay can detect Shigella from samples containing shigellae at a concentration of at least about 10,000 cfu/gram or at least about 10,000 cfu/ml.

The preparation of DNA template from fecal samples in this study was done by a simple boiling process by resuspending about 0.5 to about 2.0 grams of fecal sample in LB broth buffer at about a 1:10 ratio (weight/volume) in order to release DNA templates of pathogens from the sample into suspension for the polymerase chain reaction assay. Other diluents include brain-heart infusion broth (BHI) and Tris-EDTA buffer (10 mM Tris-HCl and 1 mM disodium EDTA). The amount of dilution can vary as long as stool, or other environmental sample is resuspended in a managable suspension for PCR sensitivity, and with the least amount of diluent. In the case of environmental samples, or samples with a low copy number of bacteria, an enrichment incubation in LB broth for 4 hours may be necessary in order to detect Shigella by PCR amplification. The samples are then boiled for about 15 minutes in order to sterilize the solution for storage at room temperature. Any other method of sterilization or storage can be used as long as the sample quality is intact and deterioration of the sample due to microbial growth is inhibited. Optionally, the boiled sample is then subjected to centrifugation at 12,000 rpm for about 15 minutes to remove large particles and the suspension containing the DNA template used in PCR assays. However, results described below indicate that centrifugation has no effect on PCR results using stool samples. The ability to use this more rapid sample preparation technique with clinical samples allows both efficiency and ease of handling.

The specific primer sets which, when mixed, form the first and second primer cocktail of the present invention were selected based a on G-C content of at least 50% or higher, and a PCR product size determined by the gap between primer pairs such that different serotypes would have distinct PCR product sizes for identification purposes. The rfc genes of *S. sonnei, S. flexneria* 2a and *S. dysenteriae* have been described previously [Klena et al., ibid.; Macpherson, et al. ibid., Morona et al., ibid.] Primer sequences derived from these genes are described in Table 1 below.

TABLE 1

| Oligonucleotide primers: | | | | |
|---|---|---|---|---|
| Names | Coordinates* | Nucleotide sequences | Origins | SEQ ID NO: |
| HS9 | F6234 | 5'-ATC-AGG-TGT-CGT-AAT-TTT-A-3' | S. sonnei rfc | SEQ ID NO:1 |
| HS57 | R7185 | 5'-GGG-CTA-AGT-TCC-CTC-3' | S. sonnei rfc | SEQ ID NO:2 |
| SF1 | F9000 | 5'-ATT-GGT-GGT-GGT-GGA-AGA-TTA-CTG-G-3' | S. flexneri 2a rfc | SEQ ID NO:3 |
| SF2 | R10095 | 5'-TTT-TGC-TCC-AGA-AGT-GAG-G-3' | S. flexneri 2a rfc | SEQ ID NO:4 |
| SF5 | F1600 | 5'-AGC-TAA-TGC-GTT-TTG-GGG-AAT-3' | S. dysenteriae 1rfc | SEQ ID NO:5 |
| SF6 | R2428 | 5'-TCC-CAA-TGA-CTG-ATA-CCA-TGG-3' | S. dysenteriae 1rfc | SEQ ID NO:6 |

*Coordinates for each primer set showing the beginning of forward (F) and reverse (R) primers reflect PCR product derived from each particular primer set. For instance, the PCR products derived from these primer sets will be equivalent to 952 bps for S. sonnei, 1096 bps for S. flexneri 1 through 5, 829 bps for S. dysenteriae.

Oligonucleotide primers were synthesized using solid-phase phosphamidiate chemistry and purified by high-pressure liquid chromatography (HPLC). Alternatively, primers may be generated by any of the standard methods of oligonucleotide synthesis and are then gel purified.

In view of the reasoning used for the design of the primer sets described in the present application, it would be within the skill of someone in the art to design other primer sets from rfc sequences which would allow the detection and indentification of other pathogenic bacteria containing rfc genes. Such bacteria include, but are not limited to, *Salmonella typhimurium, Salmonella enterica, Pseudomonas aeruginosa, E. coli, Vibrio cholera, Klebsiella pneumoniae,* to name a few.

It is not necessary that the primer sequence be 100% complementary to the priming site of the template. A primer which apposes to the template with some mismatch is within the scope of the invention if the mismatched primer-template structure can still serve as a site from which to enzymatically synthesize amplification products of the primer which are complementary to the template. One of ordinary skill in the art, without undue experimentation, will be able to design many reaction conditions, both stringent (allowing a perfect complementary sequence match between the primer and the template) and nonstringent (allowing some mismatch in the primer-template pairing) within the scope of the methods of the invention (*Nucleic Acid Hybridization, A Practical Approach.* B. D. Hames and S. J. Higgins, eds., IRL Press, Washington, 1985).

Oligodeoxynucleotides 15–30 bases long are preferable using the conditions described here. However, oligoribonucleotides, or oligodeoxynucleotides, other than 15–30 bases long may also be used. The primer must be of sufficient length to prime the synthesis of extension products in the presence of the inducing agent or polymerase.

The sequence of the primer can either comprise one or more of the deoxynucleotide DNA bases dA, dT, dC, or dG; or one or more of the ribonucleotide RNA bases A, U, C, or G; or one or more analogues of an previously cited base, e.g. I, or dI (inosine, deoxyinosine). For the purposes of the present invention ribothymidine and uridine are considered to be equivalents, as long as the polymerizing agent can use primers containing the nucleotide used. Primers may be derivatized with chemical groups to optimize their performance.

In the method of the present invention an excess of primer, polymerase and nucleoside triphosphate substrates is preferred. An "excess" of primer, polymerase or inducing agent, and nucleoside triphosphate substrates refers to an amount of each component sufficient to support amplification of template nucleic acid in a manner such that substantial amplification is not limited by the concentration of that component.

It is necessary to provide to the assay mixture an amount of required cofactors such as $Mg^{++}$, and nucleoside triphosphates dATP, dCTP, dGTP, dTTP, ATP, CTP, GTP, UTP, or other nucleoside triphosphates, herein called "triphosphate substrates", in sufficient quantity to support the degree of amplification desired. The amount of deoxynucleoside triphosphates substrates required for efficient amplification typically will be in the range of about 0.01 mM to about 1.0 mM, preferably about 0.1 mM.

With regard to PCR reactions, a wide variety of polymerases are suitable. These enzymes should exhibit thermostable activity, high fidelity and high processivity. Such enzymes are available from Boehringer Mannheim (Indianapolis, Ind., Cat. Nos. 1146 165, 1146 173, 1418 432 and 1435 094) and Perkin Elmer (Norwalk, Conn., Cat. Nos. N801-0060 and N808- 1012). The preferred enzyme is that made by Perkin Elmer.

For fractionating or resolving the PCR amplified samples, gel electrophoresis is performed such that the DNA fractions are separated. Any fractionation method or apparatus can be used such as, for example, a standard agarose mini-gel apparatus. After fractionation, the DNA products are visualized by for example, staining the DNA with ethidium bromide (EtBr) or any other method of visualizing DNA known to a person with ordinary skill in the art. The PCR products can also be detected by using labelling methods such as dioxigenis (Boehringer Mannheim, Indianapolic, Ind.).

The use of a simple DNA stain such as EtBr eliminates the inconvenience of radioisotope use and the need for radioisotope safety precautions including shielding, monitoring and specialized disposal, rendering the present assay amenable for use in clinical labs such as doctor's offices, and deployment of the system in countries that ban or limit the use of isotopes.

The method of the present invention is especially facilitated and enhanced by the use of "kits", whose components are especially adapted to be used with one another. Such kits will typically provide a carrier, compartmentalized to receive in close confinement a series of containers containing the primers or primer cocktail, the inducing agent or polymerase, and optionally a diluting solution, and the deoxynucleotides and buffers and salts necessary to conduct a particular assay.

It is understood that these descriptions, examples and embodiments are for illustrative purposes only, and that various modifications would be suggested within the spirit and purview of this application and the scope of the appended claims.

The following examples are illustrative of the practice of the invention but should not be read as limiting the scope thereof.

MATERIALS AND METHODS

Bacteria

Strains were kept on LB agar, and transferred to fresh medium periodically. LB broth was used to grow overnight cultures incubated at 37° C.

Oligonucleotide primers

The rfc genes of *S. sonnei*, *S. flexneria* 2a, and *S. dysenteriae* 1 have been described previously [Matsutani, et al. (1987) *J. Mol. Biol.* 196:445–455; Klena and Schnaitman (1993) *Mol. Microbiol.* 9:393–402; Macpherson et al. (1991) *Mol. Microbiol.* 5: 1491–1499; Morona et al. (1994) *J. Bact.* 176:733–747]. Primer sequences derived from these genes are shown in Table 1. Oligonucleotides were synthesized using solid-phase phosphoamidiate chemistry and purified by high-pressure liquid chromatography (HPLC).

DNA template preparation

DNA templates were prepared from overnight culture in LB broth by boiling bacterial cultures for 15 minutes. Alternatively, overnight cultures could also be substituted by resuspending 1–2 loopful bacteria (from agar plate) into fresh LB broth. The boiled cell suspensions were used directly as DNA template for PCR amplification, or stored at −20° C. for latter use. DNA templates were also prepared from stool samples by resuspending 0.5–2.0 grams stool into LB broth at 1:10 ratio (W/V), i.e., 1.3 gram stool was resuspended to final volume of 13.0 ml in LB broth.

DNA amplification and detection

PCR mixtures containing 10 $\mu$l 10× PCR buffer (Perkin-Elmer Inc., Norwalk, Conn.), 4 $\mu$l 25 mM $MgCl_2$, 8 $\mu$l 1.25 mM dNTP's, 50 nmole of each oligonucleotide primers, 3 $\mu$l DNA template, 0.25 unit Taq DNA polymerase (Perkin-Elmer Inc., Norwalk, Conn.), and $dH_2O$ to make up total 100 $\mu$l final volume. Amplification conditions were carried out using Perkin-Elmer 9600 thermal cycler as follow: 95° C., 3 minutes; 30 cycles of 95° C., 30 seconds; 55° C., 30 seconds; 72° C., 1 minute. The PCR products (20 $\mu$l) were analyzed by electrophoresis using 0.8% agarose gel in TBE buffer.

EXAMPLE 1

Preparing PCR DNA template from stool samples by simple boiling and centrifugation As described in materials and methods, stool samples containing *S. sonnei* were resuspended into LB broth and were subjected to boiling for 15 minutes. The boiled stool suspension was subjected to microfuge centrifugation at 12,000 rpm for 5 minutes. The top layer of centrifuged suspension was used for PCR amplification as compared to PCR amplification using DNA template prior the centrifugation. Results indicate that the intensities of PCR bands remained the same for both centrifuged and non-centrifuged DNA template (Data not shown). Thus, the simple boiling protocol used in this study can yield good quality DNA template directly from stool samples.

Utilization of rfc specific primers to differentiate among different serotypes of Shigella through amplifications The O antigen of Shigella is encoded by genes organized as the rfb operon, and a specific rfc gene encodes for O-antigen polymerase that polymerizes the O-antigen subunit into long LPS chains. It is known that the rfc gene shows very little sequence homology with other gene sequences deposited in the Genbank database (Collins et al., 1991). Thus homologous rfc sequences are present only in organisms that assemble identical, or even closely related O-antigen saccharides into LPS chains of closely related serotypes. The rfc sequences of *S. sonnei*, *S. flexneia* 2a and *S. dysenteriae* 1 are not homologous with each other. PCR oligonucleotide primer sets derived from the rfc genes of *S. sonnei* (Genbank #U34305), *S. flexneri* 2a (EMBL #X71970), and *S. dysenteriae* 1 (Genbank #L07293) were synthesized and formulated into a PCR cocktail mixture. These primer sets of different Shigella origins were designed to yield PCR product of different molecular mass as shown in Table 1. It was shown that the rfc primers of *S. flexneria* 2a (SF1 and SF2) could be used to detect all the other *S. flexneria* sertotypes with the exception of type 6 (FIG. 1). Whereas, the rfc primers of *S. sonnei* (HS9 and HS57) and *S. dysenteriae* 1 (SF5 and SF6) were specific for its own serotype detection. Thus, the primers employed for PCR amplification in this study could specifically differentiate *S. sonnei*, *S. flexneri* 1–5, and *S. dysenteriae* 1 based on the specific PCR product sizes, as shown in FIG. 1.

EXAMPLE 2

Shigella identification from stool samples by PCR amplification

Thirty six stool specimens were collected from patients with dysentery symptoms in Hanoi, Vietnam. All thirty six stool specimens were prepared for PCR assay as described in Materials and Methods above. Identification of shigellae was done by the PCR method described above using the primers described in Table 1 and compared to identification results using the conventional culturing method. Results are shown in Table 2 below.

TABLE 2

| Sample | Strains identified by PCR | Strain detected by culture |
|---|---|---|
| 11P | S. son. | S. son. |
| 19P | S. flex. | S. flex. 1b |
| 26P | S. flex. | S. flex. 4a |
| 47P | S. flex. > S. dys. | – |
| 49P | – | – |
| 52P | – | – |
| 54P | S. flex. > S. dys. | – |
| 59P | S. dys. > S. flex. | – |
| 270 | S. flex. | S. son. |
| 276 | S. flex. > S. dys. | – |
| 287 | S. dys. | – |
| 310 | S. flex., weak S. dys. | – |
| 354 | S. flex. | – |
| 363 | – | – |
| 460 | – | – |
| 494 | S. flex. | S. flex. |
| 508 | S. flex. | – |
| 517 | – | – |
| 525 | S. dys. | S. dys. |
| 531 | – | – |
| 546 | – | – |
| 582 | S. flex. > S. dys. | – |
| 649 | – | – |
| 651 | – | – |
| 661 | weak S. flex. | – |
| 688 | S. flex. >S. dys. | – |
| 464P | weak S. flex. | – |
| 466 | – | – |
| 477P | S. flex. | – |
| 509P | S. dys., weak S. flex. | – |

TABLE 2-continued

| Sample | Strains identified by PCR | Strain detected by culture |
|---|---|---|
| 512P | weak S. flex. | - |
| 516P | - | - |
| 523P | - | - |
| 540P | - | - |
| 563P | - | - |
| 587P | S. dys. | - |

Only six stool samples yielded positive shigellae isolates through conventional culturing as shown in Table 2, whereas, 24 stool samples gave positive results for the existence of different Shigella through PCR amplifications using rfc primers as shown in Table 2. Among these 24 Shigella positive stools, 8 samples showed co-existence of two different Shigella serotypes that were not detected by the culturing method. Even though there was one discrepancy derived from PCR and culturing results for sample number 270, overall, it was shown that the PCR diagnosis system is superior to conventional culturing in detecting shigellaes from stool samples.

DISCUSSION

The major obstacles of using PCR based diagnostic system to detect infectious pathogens from environmental and clinical samples involve the issues of complexity (or the ease of operation), sensitivity, and specificity for the systems. In this study, a simple boiling process was used to treat purified bacterial cultures, and stool samples. The boiled samples were centrifuged briefly to eliminate the large debris from solution and then were used as DNA templates for PCR amplifications. It was found that centrifugation had no effect on PCR results in terms of PCR product yield at different DNA template levels. Thus, simple boiling and brief centrifugation were used to prepare clean DNA templates derived from complex clinical samples, such as stool specimens.

In theory, PCR can detect a single copy of target gene after 30–40 cycles of amplification. It was estimated that the minimal Shigella to be detected through PCR amplification using primers ranges from 10 to 100 bacteria per PCR in 100 ul reaction volume. This is about equivalent to the other PCR systems used to detect either bacterial, or viral pathogens. When the target sequence exists at lower concentration level, it may not be randomly distributed through out the sample. Thus, the reason for requiring more than 1 bacterial CFU per PCR to is ensure target sequence being pipetted into reaction mixture to yield positive PCR result for every single reaction. (Matsutani, et al. (1987) *J. Mol. Biol.* 196:445–455.).

In this study, the stool samples were resuspended at 1:10 (W/V) ratio in LB broth to prepare DNA template suspension. Only 3 $\mu$l of boiled stool suspension was employed as DNA template for PCR amplification. Thus, detection limit for Shigellae in solid, or semisolid stool samples should be $3 \times 10^5$–$3 \times 10^6$ CFU/gram. It was also demonstrated that if Shigellae is presented in the stool sample below the detection level, for instance $10^4$ CFU/gram Shigellae were deliberately inoculated into normal stool sample. After enrichment incubation in LB broth for 4 hours, Shigella became detectable through PCR. Normally, stool samples originated from acute diarrheal patients contain sufficient causive infectious bacterial particles ranging from $10^5$–$10^6$ CFU/gram that are well above PCR detection limit. It was also demonstrated that DNA template prepared from stool sample could be concentrated by a factor of 10 folds or more through centrifugation in microcone-50 filter unit (Amicon Inc. Beverly, Mass.). Thus, the actual detection limit for Shigellae in stool samples could be reduced to below $10^5$ CFU/gram.

Homologous rfc sequences are present only in organisms that assemble identical, or even closely related O-antigen saccharides into LPS chains of closely related serotypes. In this study, primers derived from rfc genes of the most prominent Shigella serotypes, such as *S. sonnei, S. flexneria* 2a, and *S. dysenteriae* 1 were used for PCR amplifications. These rfc primers appear to be very specific for each individual serotype (*S. sonnei* and *S. dysenteriae* 1), and serogroup (*S. flexneria* 1, 2, 3, 4, and 5). With the exception of *S. flexneria* 6, it was shown that serotype 1 through 5 of *S. flexneria* all could be recognized by PCR amplifications using rfc primers of *S. flexneria* 2a. This is consistant with the notion that the O-LPS of *S. flexneri* type 6 does not share any structure, and genetic homology with the other serotypes in *S. flexneria* serogroup (Cheah, et al. (1991) *FEMS Microbiol. Lett.* 83: 213–218). Similarly, the rfc sequences of *S. sonnei* and *S. dysenteriae* 1 are not homologous with the rfc gene of other Shigella species.

What is claimed is:

1. A method for detecting and differentiating different serotypes of Shigella in a sample, said method comprising the steps of:
   (i) preparing the sample for a polymerase chain reaction;
   (ii) contacting said sample with
      (a) at least four different nucleotide triphosphates,
      (b) a first primer mixture that hybridizes to Shigella DNA of different Shigella species and serotypes of Shigella, and
      (c) an enzyme with polynucleotide synthetic activity, under conditions suitable for the hybridization and extension of primers by said enzyme, whereby a first DNA product is synthesized with said Shigella DNA as a template therefor, such that one or more duplex molecule(s) is formed;
   (iii) denaturing said duplex to release said first DNA product from said Shigella DNA;
   (iv) contacting said first DNA product with a reaction mixture comprising
      (a) at least four different nucleotide triphosphates,
      (b) a second primer mixture that hybridizes to said first DNA product, and
      (c) an enzyme with polynucleotide synthetic activity, under conditions suitable for the hybridization and extension of said second primer by said enzyme, whereby a second DNA product is synthesized with said first DNA product as a template therefor, such that a duplex is formed;

(v) denaturing said second DNA product from said first DNA product;

(vi) repeating steps ii–v for a sufficient number of times to achieve linear production of said first and second DNA products;

(viii) fractionating said first and second DNA products generated from said Shigella DNA; and (ix) detecting and differentiating different serotypes of Shigella by analyzing said fractionated products of step viii, wherein said first primer mixture and said second primer mixture hybridize to rfc genes.

2. The method of claim 1, wherein said sample is a biological sample selected from the group consisting of blood, stool, urine, and tissue.

3. A kit for detecting and differentiating different serotypes of Shigella in a sample using the polymerase chain reaction, comprising a carrier being compartmentalized to receive in close confinement therein one or more containers wherein:

(i) a first container or series of containers contains a primer mixture said mixture comprising primer sets which detect and differentiate different serotypes of Shigella said primer sets chosen from rfc genes of different Shigella species and serotypes such that the molecular mass of products from said polymerase chain reaction on said sample can be used to detect and differentiate different serotypes of Shigella;

(ii) a second container contains an inducing agent, (iii) a third container or series of containers contains triphosphate substrates; and (iv) a fourth container or series of containers contains buffers, cofactors and other reagents for reconstituting or diluting components of said kit.

4. An isolated Shigella rfc sequence selected from the group consisting of: SEQ ID NO: 1, SEQ ID NO: 2, SEQ ID NO: 3, SEQ ID NO: 4, SEQ ID NO: 5, and SEQ ID NO: 6.

5. A mixture of primers comprising a combination of primer sets selected from the group of primer sets consisting of: SEQ ID NO: 1 and SEQ ID NO: 2, SEQ ID NO: 3 and SEQ ID NO: 4, and SEQ ID NO: 5 and SEQ ID NO: 6.

6. A method for detecting and differentiating different serotypes of Gram negative bacteria in a sample, said method comprising the steps of:

(i) preparing the sample for a polymerase chain reaction;

(ii) contacting said sample with (a) at least four different nucleotide triphosphates, (b) a first primer mixture that hybridizes to Gram negative bacteria DNA of different species and serotypes, and (c) an enzyme with polynucleotide synthetic activity, under conditions suitable for the hybridization and extension of primers by said enzyme, whereby a first DNA product is synthesized with said Gram negative bacteria DNA as a template therefor, such that one or more duplex molecule(s) is formed;

(iii) denaturing said duplex to release said first DNA product from said Gram negative bacteria DNA;

(iv) contacting said first DNA product with a reaction mixture comprising (a) at least four different nucleotide triphosphates, (b) a second primer mixture that hybridizes to said first DNA product, and (c) an enzyme with polynucleotide synthetic activity, under conditions suitable for the hybridization and extension of said second primer by said enzyme, whereby a second DNA product is synthesized with said first DNA product as a template therefor, such that a duplex is formed;

(v) denaturing said second DNA product from said first DNA product;

(vi) repeating steps ii–v for a sufficient number of times to achieve linear production of said first and second DNA products;

(viii) fractionating said first and second DNA products generated from said Gram-negative bacteria DNA; and (ix) detecting and differentiating different serotypes of Gram negative bacteria by analyzing said fractionated products of step viii, wherein said first and second primer mixture comprise primers complementary to rfc genes of said Gram negative bacteria.

7. The method of claim 6, wherein said sample is a biological sample selected from the group consisting of blood, stool, urine, and tissue.

8. A kit for detecting and differentiating different serotypes of Gram negative bacteria in a sample using the polymerase chain reaction, said bacteria selected from the group consisting of: Salmonella, Shigella, Pseudomonas, E. coli, Vibrio, and Klebsiella, said kit comprising a carrier being compartmentalized to receive in close confinement therein one or more containers wherein:

(i) a first container or series of containers contains a primer mixture said mixture comprising primer sets which detect and differentiate different serotypes of Gram negative bacteria said primer sets chosen from rfc genes of said Gram negative bacteria such that the molecular mass of products from said polymerase chain reaction on said sample can be used to detect and differentiate different Gram negative bacteria;

(ii) a second container contains an inducing agent, (iii) a third container or series of containers contains triphosphate substrates; and (iv) a fourth container or series of containers contains buffers, cofactors and other reagents for reconstituting or diluting components of said kit.

9. The method of claim 7 wherein said stool sample is prepared for a polymerase chain reaction by a method consisting of:

(i) diluting said stool sample; and (ii) boiling said diluted stool sample.

10. The method of claim 1 wherein said first and second primer mixture is selected from the group consisting of: SEQ ID NO: 1, SEQ ID NO; 2, SEQ ID NO: 3, SEQ ID NO: 4, SEQ ID NO: 5, and SEQ ID NO: 6.

11. The kit according to claim 3 wherein said primer mixture is selected from the group consisting of; SEQ ID NO: 1, SEQ ID NO: 2, SEQ ID NO: 3, SEQ ID NO: 4, SEQ ID NO: 5, and SEQ ID NO: 6.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 19 base pairs
      (B) TYPE: Nucleic acid
      (C) STRANDEDNESS: Single
      (D) TOPOLOGY: Linear (ii) SEQUENCE DESCRIPTION: SEQ ID NO:1:

ATCAGGTGTC  GTAATTTTA                                                              19

(2) INFORMATION FOR SEQ ID NO:2:

```
        (i) SEQUENCE CHARACTERISTICS:
            (A) LENGTH: 15 base pairs
            (B) TYPE: Nucleic acid
            (C) STRANDEDNESS: Single
            (D) TOPOLOGY: Linear (ii) SEQUENCE DESCRIPTION: SEQ ID NO:2:

GGGCTAAGTT  CCCTC                                                            15

(2) INFORMATION FOR SEQ ID NO:3:

(i) SEQUENCE CHARACTERISTICS:
            (A) LENGTH: 25 base pairs
            (B) TYPE: Nucleic acid
            (C) STRANDEDNESS: Single
            (D) TOPOLOGY: Linear (ii) SEQUENCE DESCRIPTION: SEQ ID NO:3:

ATTGGTGGTG  GTGGAAGATT  ACTGG                                                25

(2) INFORMATION FOR SEQ ID NO:4:

(i) SEQUENCE CHARACTERISTICS:
            (A) LENGTH: 19 base pairs
            (B) TYPE: Nucleic acid
            (C) STRANDEDNESS: Single
            (D) TOPOLOGY: Linear (ii) SEQUENCE DESCRIPTION: SEQ ID NO:4:

TTTTGCTCCA  GAAGTGAGG                                                        19

(2) INFORMATION FOR SEQ ID NO:5:

(i) SEQUENCE CHARACTERISTICS:
            (A) LENGTH: 21 base pairs
            (B) TYPE: Nucleic acid
            (C) STRANDEDNESS: Single
            (D) TOPOLOGY: Linear (ii) SEQUENCE DESCRIPTION: SEQ ID NO:5:

AGCTAATGCG  TTTTGGGGAA  T                                                    21

(2) INFORMATION FOR SEQ ID NO:6:

(i) SEQUENCE CHARACTERISTICS:
            (A) LENGTH: 21 base pairs
            (B) TYPE: Nucleic acid
            (C) STRANDEDNESS: Single
            (D) TOPOLOGY: Linear (ii) SEQUENCE DESCRIPTION: SEQ ID NO:6:

TCCCAATGAC  TGATACCATG  G                                                    21
```